United States Patent
Peck et al.

(10) Patent No.: US 10,533,179 B2
(45) Date of Patent: Jan. 14, 2020

(54) ANTAGONISTIC CTLA-4 APTAMERS AND APPLICATIONS THEREOF IN ENHANCING IMMUNE ACTIVITY

(71) Applicants: Academia Sinica, Taipei (TW); National Taiwan University, Taipei (TW); Taipei Medical University, Taipei (TW)

(72) Inventors: Konan Peck, Taipei (TW); Pan-Chyr Yang, Taipei (TW); Yi-Chung Chang, Taipei (TW); Bo-Tsang Huang, Taipei (TW); Shauh-Der Yeh, Taipei (TW)

(73) Assignees: Academia Sinica, Taipei (TW); National Taiwan University, Taipei (TW); Taipei Medical University, Taipei (TW)

( * ) Notice: Subject to any disclaimer, the term of this patent is extended or adjusted under 35 U.S.C. 154(b) by 113 days.

(21) Appl. No.: 15/500,345

(22) PCT Filed: Jul. 31, 2015

(86) PCT No.: PCT/US2015/043133
§ 371 (c)(1),
(2) Date: Jan. 30, 2017

(87) PCT Pub. No.: WO2016/019255
PCT Pub. Date: Feb. 4, 2016

(65) Prior Publication Data
US 2017/0211067 A1    Jul. 27, 2017

Related U.S. Application Data

(60) Provisional application No. 62/031,406, filed on Jul. 31, 2014.

(51) Int. Cl.
| C12N 15/115 | (2010.01) |
| C12N 15/113 | (2010.01) |
| A61K 31/711 | (2006.01) |
| A61K 9/00 | (2006.01) |
| A61K 31/713 | (2006.01) |
| A61K 47/60 | (2017.01) |

(52) U.S. Cl.
CPC ......... *C12N 15/115* (2013.01); *A61K 9/0019* (2013.01); *A61K 31/711* (2013.01); *A61K 31/713* (2013.01); *A61K 47/60* (2017.08); *C12N 15/1138* (2013.01); *C12N 2310/16* (2013.01); *C12N 2310/351* (2013.01)

(58) Field of Classification Search
None
See application file for complete search history.

(56) References Cited

U.S. PATENT DOCUMENTS

2006/0246123 A1    11/2006  Gilboa et al.
2013/0209514 A1    8/2013   Gilboa et al.

FOREIGN PATENT DOCUMENTS

| JP | 2006-522101 A | 9/2006 |
| JP | 2007-525177 A | 9/2007 |
| WO | WO 2013/010749 A1 | 1/2013 |
| WO | 2013/047844 A | 3/2015 |

OTHER PUBLICATIONS

Oberthur et al., Nature Communications, 2015, 6: 1-11.*
Long et al., RNA, 2008, 14: 2504-2512.*
Herrmann et al., CTLA4 aptamer delivers STAT3 siRNA to tumor-associated and malignant T cells. J Clin Invest. Jul. 2014;124(7):2977-87. doi: 10.1172/JCI73174. Epub Jun. 2, 2014. Erratum in: J Clin Invest. Jun. 2015;125(6):2547. Swiderski, Piotr [Added].
Huang et al., A CTLA-4 Antagonizing DNA Aptamer with Antitumor Effect. Mol Ther Nucleic Acids. Sep. 15, 2017;8:520-528. doi: 10.1016/j.omtn.2017.08.006. Epub Aug. 15, 2017. Supplemental Information.
Santulli-Marotto et al., Multivalent RNA aptamers that inhibit CTLA-4 and enhance tumor immunity. Cancer Res. Nov. 1, 2003;63(21):7483-9.

* cited by examiner

*Primary Examiner* — Ileana Popa
(74) *Attorney, Agent, or Firm* — Polsinelli

(57) ABSTRACT

Aptamers that bind to and inhibit CTLA-4 and uses thereof in enhancing immune activities, and treating cancer and HIV infection are provided.

17 Claims, 15 Drawing Sheets

Specification includes a Sequence Listing.

B.

c.

A

B

ANTAGONISTIC CTLA-4 APTAMERS AND APPLICATIONS THEREOF IN ENHANCING IMMUNE ACTIVITY

CROSS-REFERENCE TO RELATED APPLICATIONS

The present application is a national stage filing under 35 U.S.C. § 371 of International Application No. PCT/US2015/043133, filed Jul. 31, 2015, which claims priority under 35 U.S.C. § 119(e) to U.S. Provisional Application No. 62/031,406, filed Jul. 31, 2014, the entire content of each of which is incorporated by reference herein in its entirety.

BACKGROUND OF INVENTION

Cancer is the most important disease that causes human death and tremendous financial cost. According to a WHO report in 2004, over 7.4 million lives worldwide were lost to this illness and the victims are still increasing yearly (Abou-Alfa, G. K., et al. (2006), *J Clin Oncol* 24, 4293-4300. The primary treatments for cancer are surgery, chemotherapy, and radiotherapy. However, these traditional therapies cause serious side effects and kill normal cells as well.

For this reason, targeted therapies were developed and proved to be effective in treating several types of cancer effectively (Van Cutsem, E., et al. (2009), *N Engl J Med* 360, 1408-1417, Klein, S. and Levitzki A. (2007), *Adv Cancer Res* 97, 295-319). However, there are few tumor specific markers and only few targeted therapies were successfully applied in the clinic (Jain, R. K., et al. (2009), *Nat Rev Clin Oncol* 6, 327-3384, Gazdar, A. F. (2009), *Oncogene* 28 Suppl 1, S24-31). Moreover, many studies have shown that the genomic instability facilitates resistance to targeted therapies (Dassie, J. P., et al. (2009), *Nat Biotechnol* 27, 839-849, Sica, A., Schioppa, T., Mantovani, A., and Allavena, P. (2006), *Eur J Cancer* 42, 717-727). More recently, reports have indicated that the surrounding tumor microenvironment is strongly associated with tumor progression, particularly immune evasion (Pollard, J. W. (2004), *Nat Rev Cancer* 4, 71-78, de Visser, K. E., and Coussens, L. M. (2006), *Contrib Microbiol* 13, 118-137, Stewart, T. J., and Abrams, S. I. (2008), *Oncogene* 27, 5894-5903, Joyce, J. A., and Pollard, J. W. (2009), *Nat Rev Cancer* 9, 239-252).

Several cell types have been suggested to play key roles in the tumor microenvironment and are involved in tumor progression, including tumor-associated macrophages (TAM), regulatory T cells (Treg), natural killer (NK) cells and $CD8^+$ T-cells (Solinas, G., Germano, G., Mantovani, A., and Allavena, P. (2009), *J Leukoc Biol* 86, 1065-1073, Zou, W. (2006), *Nat Rev Immunol* 6, 295-307, Whiteside, T. L. (2006), *Cancer Treat Res* 130, 103-124, Coffelt, S. B., Hughes, R., and Lewis, C. E. (2009), *Biochim Biophys Acta* 1796, 11-18). NK and $CD8^+$ T-cells are two major effective cell types to eradicate abnormal tumor cells by cell-mediated cytotoxicity. Treg cells represent a small fraction (5-6%) of the overall $CD4^+$ T cells (Wang, R. F., Peng, G., and Wang, H. Y. (2006), *Semin Immunol* 18, 136-142) and is another major regulatory cell type in tumor microenvironment. Under normal circumstances, Treg cells protect the host from self-reactive T-cells and, therefore, prevent the formation of autoimmune disease (Corthay, A. (2009), *Scand J Immunol* 70, 326-336). However, in tumor microenvironment, Treg can secrete cytokines, such as IL-10 and TGF-β, to inhibit the function of tumor-targeted innate (NK cells) and adaptive ($CD8^+$ T-cells) immune response (Bingle, L., Brown, N. J., and Lewis, C. E. (2002), *J Pathol* 196, 254-265) and protect tumor cells from immune clearance (Andrew, G. et al. (2006), *J Immunol* 177, 896-904).

One protein receptor that can down-regulate the immune system in the tumor microenvironment is Cytotoxic T-Lymphocyte Antigen 4 (CTLA-4), also known as cluster of differentiation 152 (CD152). CTLA-4 is found on the surface of T cells, which lead the cellular immune attack on antigens. While the T cell attack can be turned on by stimulating the CD28 receptor on T cells, it can be turned off by stimulating the CTLA4 receptor.

While antibodies are commonly used to target disease proteins, they have their limitations, including high production costs, low stability, and are restricted in many cases as to the epitopes they can target. Aptamers have several advantages that make it suitable for therapeutic application such as lower molecular weight that allows easier penetration through tissues, low cost in chemical synthesis, established modification methods and high stability. It is therefore of great interest to develop suitable aptamers having high affinity to a target protein.

SUMMARY OF INVENTION

The present disclosure is based at least in part, on the unexpected discoveries that a nucleotide aptamer targeting CTLA-4 (CA21) successfully suppressed the growth of lung tumor cells by over 70% in a syngeneic mouse model.

Accordingly, one aspect of the present disclosure features a nucleic acid aptamer binding to CTLA-4. The aptamer comprises a nucleic acid sequence that is at least 85% (e.g., 90%, or 95%) identical to (i) GATGGTGAAAATGGGCCTAGGGTGGACGGT (SEQ ID NO: 1), (ii) GATGACTGGATGCAAAAATGCTGTGGGGTA (SEQ ID NO: 6), (iii) GTCCACACTCAGAAAACAGAATAGGGGGTA (SEQ ID NO: 7), or (iv) CGATCGAAAATGTCCAGGGAGTTGTCTGTA (SEQ ID NO: 8). Such an anti-CTLA-4 aptamer may bind to CTLA-4 with a dissociation constant (Kd) lower than 20 nM. In one example, the anti-CTLA4 aptamer may comprise the nucleic acid sequence of GATGGTGAAAATGGGCCTAGGGTGGACGGT (SEQ ID NO: 1), GATGACTGGATGCAAAAATGCTGTGGGTA (SEQ ID NO: 6), GTCCACACTCAGAAAACAGAATAGGGGGTA (SEQ ID NO: 7), or CGATCGAAAATGTCCAGGGAGTTGTCTGTA (SEQ ID NO: 8). Such an anti-CTLA4 aptamer may be the nucleic acid of TCCCTACGGCGCTAAC-GATGGTGAAAA TGGGCCTAGGGTGGACGG TGC-CACCGTGCTACAAC (SEQ ID NO: 2), TCCCTACG-GCGCTAACGATGACTGGATGCAAAAATGCTGTGGG-GTAGCCACCGTGC TACAAC (SEQ ID NO: 3), TCCCTACGGCGCTAACGTCCACACTCAGAAAACA-GAATAGGGGGTAGCCACCGTGC TACAAC (SEQ ID NO: 4), or TCCCTACGGCGCTAACCGATCGAAAAT-GTCCAGGGAGTTGTCTGTAGCCACCGTGCT ACAAC (SEQ ID NO: 5).

Any of the anti-CTLA-4 aptamers described herein may be conjugated with polyethylene glycol (PEG), which may have a molecular weight ranging from 30 kDa to 50 kDa, e.g., 40 kDa. In some examples, the PEG is conjugated to the 3' end of the aptamer.

In another aspect, the present disclosure provides a pharmaceutical composition comprising any of the anti-CTLA-4 aptamers as described herein and a pharmaceutically acceptable carrier.

In yet another aspect, the present disclosure provides a method for treating cancer (e.g., lung cancer, melanoma, colorectal cancer, or renal-cell cancer), the method comprising administering (e.g., intravenously) to a subject in need thereof an effective amount of any of the pharmaceutical compositions as described herein, which comprises a anti-CTLA-4 aptamer as also described herein.

In some examples, the subject to be treated by the method described herein is a human patient, e.g., a human patient having, suspected of having, or at risk for cancer.

Further, the present disclosure features a method of enhancing immune activity in a subject, the method comprising administering (e.g., intravenously) to a subject in need thereof an effective amount (e.g., an amount sufficient to increase T cell activation) of any of the pharmaceutical compositions described herein, which comprises a anti-CTLA-4 aptamer as also described herein. In some examples, the subject can be a human patient having, suspected of having, or at risk for cancer (e.g., lung cancer, melanoma, colorectal cancer, or renal-cell cancer). In other examples, the subject is a human patient having or suspected of having HIV infection.

Also within the scope of the present disclosure are (a) pharmaceutical compositions for use in treating cancer (e.g., lung cancer, melanoma, colorectal cancer, or renal-cell cancer) or HIV infection, wherein the pharmaceutical composition comprises an anti-CTLA-4 nucleic acid aptamer as described herein, e.g., a nucleic acid comprising a nucleic acid sequence that is at least 85% (e.g., 90%, or 95%) identical to (i) GATGGTGAAAATGGGCCTAGGGTG-GACG GT (SEQ ID NO: 1), (ii) GATGACTGGATG-CAAAAATGCTGTGGGGTA (SEQ ID NO: 6), (iii) GTC-CACACTCAGAAAACAGAATAGGGGGTA (SEQ ID NO: 7), or (iv) CGATCGAA AATGTCCAGGGAGTT-GTCTGTA (SEQ ID NO: 8); and a pharmaceutically acceptable carrier; and (b) use of the CTLA-4 aptamer for manufacturing a medicament for treating cancer (e.g., lung cancer, melanoma, colorectal cancer, or renal-cell cancer) or HIV infection.

The details of one or more embodiments of the invention are set forth in the description below. Other features or advantages of the present invention will be apparent from the following drawings and detailed description of several embodiments, and also from the appended claims.

DETAILED DESCRIPTION OF INVENTION

Figure 1:
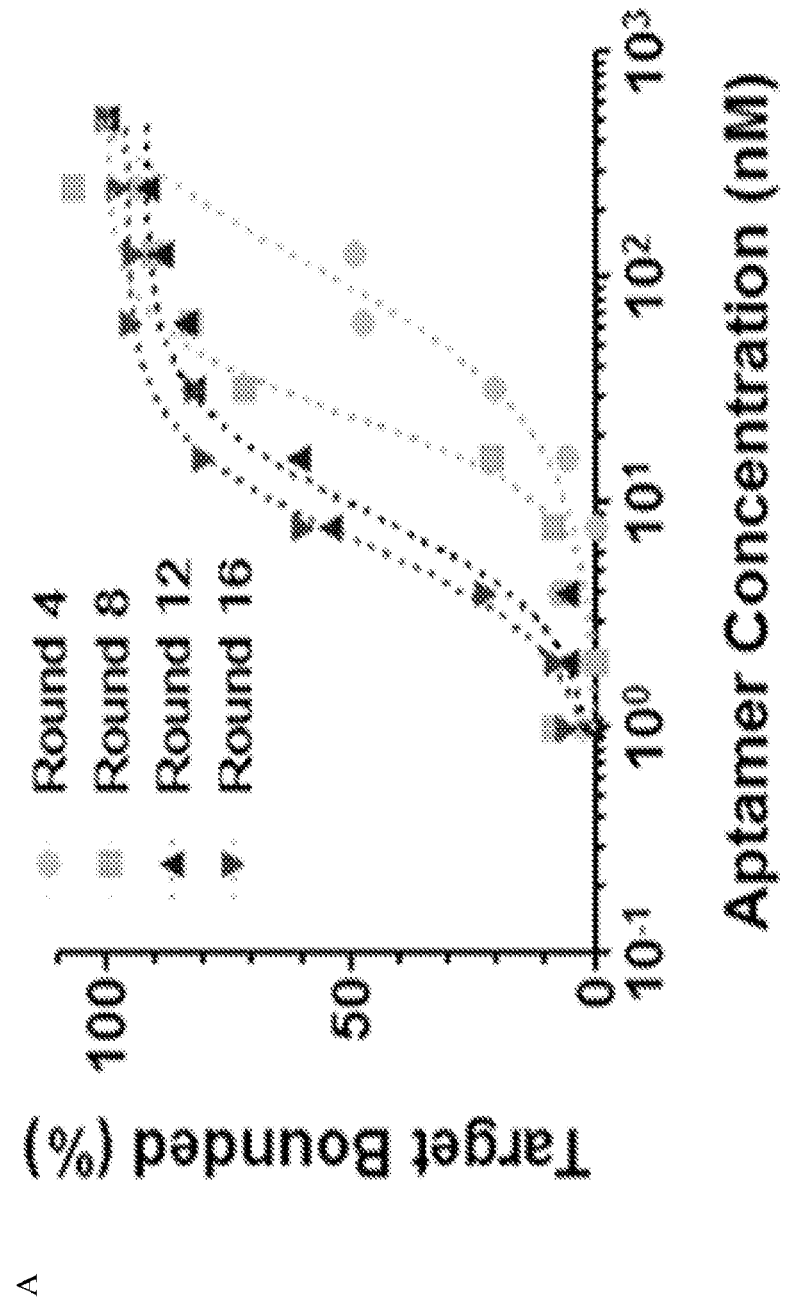
FIG. 1 includes diagrams showing the binding affinity increasing by SELEX evolution. Panel A is a chart showing binding activities of aptamers to CTLA-4 at various concentrations. Aptamer pools in round 4, 8, 12, 16 against CTLA-4 were amplified and follow by 2 fold of serial dilution which started from 500 nM. Ten dosage points were analyzed for each of the selected pool by incubation with CTLA-4 transfected wild-type 293T cells. The bounded aptamers were quantified by RT-qPCR. The result is shown in the XY plot of panel A. The circle indicates the result for round 4, the square for round 8, the triangle pointing up for round 12 and the inverted triangle for round 16. The dashed lines indicate the fit curves for each of the pools. The dissociation constant for round 4, 8, 12, 16 were 120.7 nM, 24 nM, 8.8 nM and 6.6 nM, respectively. Panels B-I show FACS analysis diagrams of aptamer binding activities to CTLA-4 expressed on wild-type 293T cells. Aptamer pools from SELEX round 4, 8, 12 and 16 were labeled with AlexaFluor 647 by PCR. The labeled aptamers were incubated with either wild type 293T cells (panels B, C, D and E) or CTLA-4 transfected wild-type 293T cells (panels F, G, H, I). Flow cytometry was used to evaluate the binding signal. Panels B, C, D and E show the result of wild type 293T cells and panels F, G, H and I show the result of transfected 293T cells.
Figure 1:
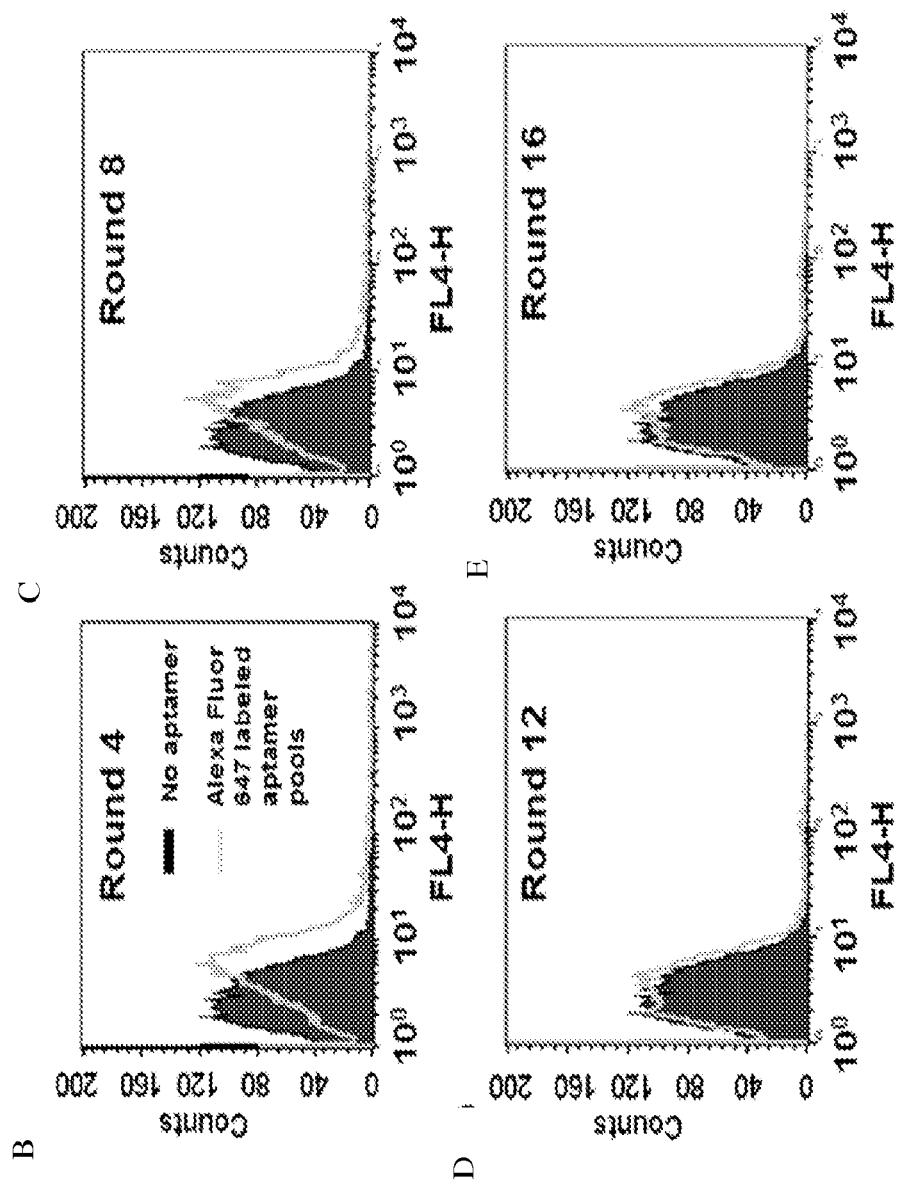
Figure 1:
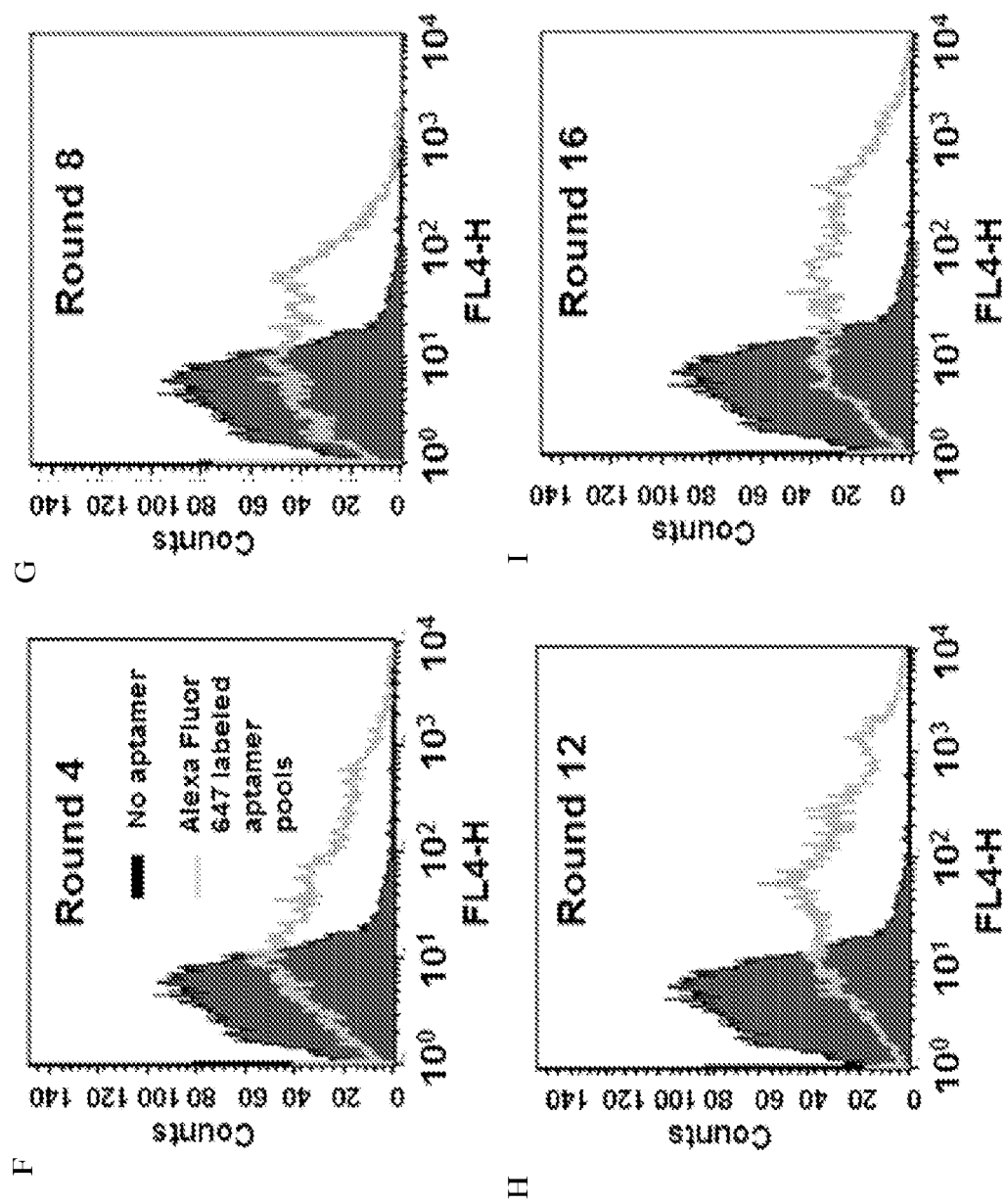

The present disclosure is based on the development of nucleic acid aptamers (e.g., CA21) that specifically bind and inhibit CTLA-4 and the unexpected results that such nucleic acid aptamers successfully suppressed the growth of cancer cells by over 70% in a syngeneic mouse model. The anti-CTLA4 aptamer treatment did not affect mouse body weight, suggesting that the aptamer is not toxic. Thus, anti-CTLA-4 aptamers such as CA21 would be effective in enhancing immune activity and/or reducing cancer growth.

Accordingly, described herein are anti-CTLA-4 aptamers such as CA21, pharmaceutical compositions comprising such, and methods for enhancing immune activity and/or treating diseases such as cancer and HIV infection with the anti-CTLA-4 aptamers disclosed herein.

Anti-CTLA-4 Nucleic Acid Aptamers

Described herein are nucleic acid aptamers that bind to CTLA-4 and inhibits it activity (anti-CTLA-4 aptamers), thereby enhancing immune activity such as T cell activity. Accordingly, the anti-CTLA-4 aptamers can be used to enhance immune responses, for example, T cell responses, and thus benefit immunotherapy of cancer.

A nucleic acid aptamer as used herein refers to a nucleic acid molecule (DNA or RNA) having a binding activity for a particular target molecule (e.g., CTLA-4), and thus inhibit its activity. The anti-CTLA-4 aptamer of the present disclosure, in linear or circular form, may be an RNA, a DNA (e.g., a single-stranded DNA), a modified nucleic acid, or a mixture thereof. The anti-CTLA-4 aptamers may be non-naturally molecules (e.g., containing a nucleotide sequence not existing in native genes or containing modified nucleotides not existing in nature). Alternatively or in addition, the anti-CTLA-4 aptamers may not contain a nucleotide sequence that encodes a functional peptide.

CTLA-4, referring to cytotoxic T-lymphocyte-associated protein 4 (also known as CD152), is a receptor expressed on T cells that negatively regulates T cell activity. As an example, the amino acid sequence of a human CTLA-4 is provided under GenBank accession number AAH69566.

In some embodiments, the anti-CTLA-4 nucleic acid aptamer disclosed herein may comprise a nucleotide sequence at least 70% (e.g., 80%, 85%, 90%, 95%, or 98%) identical to 5'-GATGGTGAAAATGGGCCTAGGGTG-GACGGT-3' (SEQ ID NO: 1). In some examples, the anti-CTLA-4 nucleic acid aptamer disclosed herein may comprise a nucleotide sequence at least 85% identical to the nucleic acid sequence of SEQ ID NO: 1. In some examples, the anti-CTLA-4 aptamer comprises the nucleotide sequence of 5'-GATGGTGAAAATGGGCCTAG GGTG-GACGGT-3' (SEQ ID NO: 1). In a particular example, the anti-CTLA-4 aptamer consists of the nucleotide sequence of SEQ ID NO:1 or SEQ ID NO:2.

In some embodiments, the anti-CTLA4 nucleic acid aptamer disclosed herein may comprise a nucleotide sequence at least 70% (e.g., 80%, 85%, 90%, 95%, or 98%) identical to the regions in boldface of the following sequences:

(a)
(SEQ ID NO: 3)
TCCCTACGGCGCTAACGATGACTGGATGCAAAAATGCTGTGGGGT AGCCACCGTGCTACAAC;

(b)
(SEQ ID NO: 4)
TCCCTACGGCGCTAACGTCCACACTCAGAAAACAGAATAGGGGGT AGCCACCGTGCTACAAC;
or (c)
(SEQ ID NO: 5)
TCCCTACGGCGCTAACCGATCGAAAATGTCCAGGGAGTTGTCTGTA GCCACCGTGCTACAAC.

In some examples, the anti-CTLA-4 nucleic acid aptamer disclosed herein may comprise a nucleotide sequence at least 85% identical to the nucleic acid sequence of SEQ ID NO: 3, 4, or 5. In some examples, the anti-CTLA-4 aptamer comprises the nucleotide sequence of SEQ ID NO:3, 4, or 5, or the regions in boldface therein. In a particular example, the anti-CTLA-4 aptamer consists of the nucleotide sequence of SEQ ID NO:3, 4, or 5, or the boldfaced region therein.

The "percent identity" of two nucleic acids is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST nucleotide searches can be performed with the NBLAST program, score=100, word-length-12 to obtain nucleotide sequences homologous to the nucleic acid molecules of the invention. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In other embodiments, the anti-CTLA-4 aptamers described herein may contain up to 8 (e.g., up to 7, 6, 5, 4, 3, 2, or 1) nucleotide variations as compared to the nucleotide sequence of 5'-GATGGTGAAAATGGGC-CTAGGGTGGACGGT-3' (SEQ ID NO: 1). Positions where such variations can be introduced can be determined based on, e.g., the secondary structure of CA21, which comprises the reference nucleotide sequence (see FIG. 3B).

In some examples, the anti-CTLA-4 aptamers may contain a primer site at the 5' end, the 3' end, or both. In one example, the anti-CTLA-4 aptamer has the nucleotide sequence of (SEQ ID NO: 2)
*TCCCTACGGCGCTAAC*GATGGTGAAAATGGGCCTAGGGTGGACGG
*TGCCACCGTGCTACAAC*-3', in which the underlined/italic flanking sequences refer to the 5' and 3' primer sites. See also the non-boldfaced regions in SEQ ID NO:3, 4, or 5.

Any of the anti-CTLA-4 aptamers disclosed herein may contain up to 200 nucleotides (nts), e.g., 150 nts, 100 nts, 80 nts, 70 nts, 60 nts. 50 nts, 40 nts, or 30 nts. In some examples, the anti-CTLA-4 aptamer may contain nucleotides ranging from 30-150 nts, 30-100 nts, 30-80 nts, 30-70 nts, 30-60 nts, 30-50 nts, or 30-40 nts.

In some embodiments, the anti-CTLA-4 aptamers described herein may bind to CTLA-4 (e.g., human CTLA-4) with a dissociation constant (Kd) lower than 20 nM (e.g., 15 nM, 10 nM, 5 nm, 1 nm, or less). The anti-CTLA-4 aptamer may specifically bind human CTLA-4. Alternatively, the aptamer may bind to CTLA-4 molecules from different species (e.g., human and mouse). When binding to a CTLA-4 molecule expressed on T cell surface, such an aptamer may inhibit the activity of CTLA-4 (thus increase T cell activity) by at least 20% (e.g., 40%, 50%, 80%, 100%, 2-fold, 5-fold, 10-fold, 100-fold, or 1,000-fold). The inhibitory activity of an anti-CTLA-4 aptamer on CTLA-4 (and thus the activation in enhancing T cell activity) may be determined by, e.g., those described in the Examples below.

In some embodiments, the anti-CTLA-4 aptamers described herein may contain non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the aptamer described herein has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

In another example, the aptamers described herein include one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted C1 to C10 alkyl or C2 to C10 alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim. Acta, 1995, 78, 486-504.

Alternatively or in addition, aptamers described herein may include one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of aptamer molecules to their targeting sites. These include 5-substituted pyrimidines, 6-azapyrimidines and N-2, N-6 and O-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

Any of the aptamers described herein can be prepared by conventional methods, e.g., chemical synthesis or in vitro transcription. Their intended bioactivity as described herein can be verified by, e.g., those described in the Examples below. Vectors for expressing any of the anti-CTLA-4 aptamers are also within the scope of the present disclosure.

Any of the aptamers described herein may be conjugated to one or more polyether moieties, such as polyethylene glycol (PEG) moieties, via covalent linkage, non-covalent linkage, or both. Accordingly, in some embodiments, aptamers described herein are pegylated. The disclosure is not meant to be limiting with respect to a PEG moiety of a specific molecular weight. In some embodiments, the polyethylene glycol moiety has a molecular weight ranging from 5 kDa to 100 kDa, 10 kDa to 80 kDa, 20 kDa to 70 kDa, 20 kDa to 60 kDa, 20 kDa to 50 kDa, or 30 kDa to 50 kDa. In some examples, the PEG moiety has a molecular weight of 40 kDa. The PEG moiety conjugated to the anti-CTLA-4 aptamer described herein can be linear or branched. It may be conjugated to the 5' end of the nucleic acid aptamer, the 3' end of the aptamer, or both. When needed, the PEG moiety can be conjugated to the 3' end of the nucleic acid aptamer covalently.

Methods for conjugating PEG moieties to nucleic acids are known in the art and have been described previously, for example, in PCT Publication No. WO 2009/073820, the relevant teachings of which are incorporated by reference herein. It should be appreciated that the PEG conjugated nucleic acid aptamers and methods for conjugating PEG to the nucleic acid aptamers described herein, are exemplary and not meant to be limiting.

The present disclosure also provides dimers of any of the anti-CTLA-4 nucleic acid aptamers described herein. In some embodiments, an anti-CTLA-4 aptamer dimer comprises two anti-CTLA-4 aptamers linked by a suitable polymer moiety, which can be a PEG moiety as those described herein. Either one or both of the two aptamers in a dimer may comprise a nucleotide sequence of SEQ ID NOs: 1-2. Alternatively, one or both of the two aptamers in a dimer may comprise a nucleotide sequence of SEQ ID NO:3, 4, or 5, or the boldfaced region therein. The two anti-CTLA-4 aptamers may be identical or different. For example, one or both of the anti-CTLA-4 aptamers may comprise (SEQ ID NO: 1). In another example, the anti-CTLA-4 aptamer dimer as described herein may have one aptamer comprising (SEQ ID NO: 1) and another aptamer comprising (SEQ ID NO: 2).

In some embodiments, the polymer moiety of any of the anti-CTLA-4 aptamer dimers provided herein is PEG, which may have a molecular weight as described herein.

In some embodiments, the anti-CTLA-4 aptamer dimers provided herein comprise aptamers that are linked to the polymer moiety via a linker. In one example, the first aptamer is linked to the polymer moiety via a linker. In another example, the second aptamer is linked to the polymer moiety via a linker. In yet another example, the first aptamer and the second aptamer is linked to the polymer moiety via a linker. A "linker" as used herein, refers to a chemical moiety linking two molecules or moieties. In some examples, the linker comprises one or more nucleotides, which may be deoxyribonucleotides. In some examples the nucleic linker is from 1 to 50 nucleotides in length. Such linkers may be from 1 to 5, from 1 to 10, from 1 to 15, from 1 to 20, from 1 to 30, from 1 to 40, from 10 to 15, from 10 to 20, from 10 to 30, from 10 to 40, from 10 to 50, from 20 to 30, from 20 to 40, from 20 to 50, from 30 to 40, from 30 to 50, or from 40 to 50 nucleotides in length. In some examples, the linker is 11 nucleotides in length. The linker may comprise adenine (A), cytosine (C), thymine (T) and/or guanine (G). In some examples, the linker comprises a polyT fragment. A "polyT fragment" refers to a stretch of 2 or more consecutive thymine (T) nucleotide residues. For example, the polyT linker may comprise from 2 to 50 T residues. In some examples, the polyT linker is from 2 to 40, from 2 to 35, from 2 to 30, from 2 to 25, from 2 to 20, from 5 to 15, or from 10 to 15 nucleotides in length. In some embodiments, the poly T linker comprises 11 consecutive thymine (T) nucleotides.

Pharmaceutical Compositions

Any of the anti-CTLA-4 aptamers or PEG conjugates as described herein can be mixed with a pharmaceutically acceptable carrier to form a pharmaceutical composition for use, e.g., in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. See, e.g., Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In some examples, the pharmaceutical composition described herein comprises liposomes containing the CTLA-4 binding aptamers (or a vector carrying the nucleotide sequence of the aptamer), which can be prepared by methods, such as those described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The anti-CTLA-4 aptamers may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the anti-CTLA-4 aptamer, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic anti-CTLA-4 aptamer compositions may be placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .im, particularly 0.1 and 0.5 .im, and have a pH in the range of 5.5 to 8.0.

The emulsion compositions can be those prepared by mixing anti-CTLA-4 aptamers with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Methods of Treatment

Any of the anti-CTLA-4 aptamers (including PEG conjugates) described herein can be used to enhance immune activity, particularly T cell activity, thereby effective in treating cancer or infectious diseases such as viral (e.g., HIV) infection or bacterial infection.

To practice the method disclosed herein, an effective amount of the pharmaceutical composition described herein that contains at least one anti-CTLA-4 aptamer can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the anti-CTLA-4 aptamer-containing composition as described herein can be aerosolized using a fluorocarbon formulation and a metered dose inhaler, or inhaled as a lyophilized and milled powder.

As used herein, "an effective amount" refers to the amount of each active agent required to confer therapeutic effect on the subject, either alone or in combination with one or more other active agents. In some embodiments, the therapeutic effect is reduced tumor burden, reduction of cancer cells, or increased immune activity. Determination of whether an amount of the CTLA-4 binding aptamers achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a target disease/disorder. Alternatively, sustained continuous release formulations of a CTLA-4 binding aptamer may be appropriate. Various formulations and devices for achieving sustained release are known in the art.

In one example, dosages for a CTLA-4 binding aptamer as described herein may be determined empirically in individuals who have been given one or more administration(s) of the CTLA-4 binding aptamer. Individuals are given incremental dosages of the antagonist. To assess efficacy of the antagonist, an indicator of the disease/disorder can be followed.

Generally, for administration of any of the anti-CTLA-4 aptamers described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 2 mg/kg, followed by a weekly maintenance dose of about 1 mg/kg of the CTLA-4 binding aptamer, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the CTLA-4 binding aptamer used) can vary over time.

In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of a CTLA-4 binding aptamer as described herein will depend on the specific CTLA-4 binding aptamer, CTLA-4 binding aptamers, the type and severity of the disease/disorder, whether the CTLA-4 binding aptamer is administered for preventive or therapeutic purposes, previous therapy, the patient's clinical history and response to the antagonist, and the discretion of the attending physician. A clinician may administer a CTLA-4 binding aptamer, until a dosage is reached that achieves the desired result. In some embodiments, the desired result is a decrease in tumor burden, a decrease in cancer cells, or increased immune activity. Methods of determining whether a dosage resulted in the desired result would be evident to one of skill in the art. Administration of one or more CTLA-4 binding aptamers can be continuous or intermittent, depending, for example, upon the recipient's physiological condition, whether the purpose of the administration is therapeutic or prophylactic, and other factors known to skilled practitioners. The administration of a CTLA-4 binding aptamer may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, the CTLA-4 binding aptamers described herein are administered to a subject in need of the treatment at an amount sufficient to reduce tumor burden or cancer cell growth, or HIV proliferation by at least 5% (e.g., 10%, 20%, 30%, 40%, 50%, 60%, 70%, 80%, 90% or greater) in vivo. In other embodiments, the CTLA-4 binding aptamers are administered in an amount effective in reducing the activity level of CTLA-4 by at least 5% (e.g., 10%, 20%, 30%, 40%, 50%, 60%, 70%, 80%, 90% or greater). In other embodiments, the CTLA-4 binding aptamers are administered in an amount effective in increasing immune activity by at least 5% (e.g., 10%, 20%, 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularlly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble CTLA-4 binding aptamers can be administered by the drip method, whereby a pharmaceutical formulation containing the CTLA-4 binding aptamer and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the CTLA-4 binding aptamer, can be dissolved and administered in a pharmaceutical excipient such as Water-for-Injection, 0.9% saline, or 5% glucose solution.

In one embodiment, a CTLA-4 binding aptamer is administered via site-specific or targeted local delivery techniques. Examples of site-specific or targeted local delivery techniques include various implantable depot sources of the CTLA-4 binding aptamer or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338.

Therapeutic compositions containing a polynucleotide (e.g., the CTLA-4 binding aptamers described herein or vectors for producing such) are administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol.

The subject to be treated by the methods described herein can be a mammal, such as a farm animals, sport animals, pets, primates, horses, dogs, cats, mice and rats. In one example, the subject is a human. The anti-CTLA-4 aptamer-containing composition may be used for enhancing immune activity, for example, T cell activity, in a subject in need of the treatment. In some examples, the subject may be a human patient having, suspected of having, or at risk for a cancer, such as lung cancer, melanoma, colorectal cancer, or renal-cell cancer. In other examples, the subject can be a human patient having or suspected of having HIV infection. Such a patient can also be identified by routine medical practices.

A subject having a target disease or disorder (e.g., cancer or viral infection such as HIV infection, or bacterial infection) can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors associated with that disease/disorder. Such a subject can also be identified by routine medical practices.

The particular dosage regimen, i.e., dose, timing and repetition, used in the method described herein will depend on the particular subject (e.g., a human patient) and that subject's medical history.

In some embodiments, the anti-CTLA-4 aptamer may be co-used with another suitable therapeutic agent (e.g., an anti-cancer agent or an anti-HIV agent). Alternatively or in addition, the anti-CTLA-4 aptamer may also be used in conjunction with other agents that serve to enhance and/or complement the effectiveness of the agents.

Treatment efficacy for a target disease/disorder can be assessed by, e.g., a method described in the Examples below.

Kits for Use in Alleviating a Target Disease

The present disclosure also provides kits for use in enhancing immune activity (e.g., T cell activity), alleviating cancer (e.g., lung cancer, melanoma, colorectal cancer, or renal-cell cancer), and/or treating or reducing the risk for HIV infection. Such kits can include one or more containers comprising an aptamer that binds CTLA-4, e.g., any of those described herein.

In some embodiments, the kit can comprise instructions for use in accordance with any of the methods described herein. The included instructions can comprise a description of administration of the aptamer to treat, delay the onset, or alleviate a target disease as those described herein. The kit may further comprise a description of selecting an individual suitable for treatment based on identifying whether that individual has the target disease. In still other embodiments, the instructions comprise a description of administering the aptamer to an individual at risk of the target disease.

The instructions relating to the use of a CTLA-4 binding aptamer generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder associated with cancer, such as those described herein. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a CTLA-4 binding aptamer as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Screening for Anti-CTLA-4 Aptamers by Immunoprecipitate-SELEX

The present study employed methods for systematic evolution of ligands by exponential enrichment (SELEX), in which binding molecules are selected from a large and diverse library of nucleic acids (either DNAs or RNAs). See, e.g., Mol. Cell Biol (Oliphant A. R., et al., 1989); Science (Tuerk C. et al., 1990); Nature (Ellington A. D., et al., 1990).

To increase the successful rate of aptamer selection, a selection strategy combined with Immunoprecipitate-SELEX (IP-SELEX) and cell-based SELEX was adopted. IP-SELEX can largely reduce the non-specific aptamer from the pool and, on the other hand, cell-based SELEX can reduce the aptamers which fail to recognize target protein on cell membrane. Sixteen rounds of SELEX procedure were performed for FOLR-2 and CTLA-4, respectively. The IP-SELEX was used in the $2^{nd}$, $3^{rd}$ and $4^{th}$ rounds, while cell-based SELEX was in the rest rounds. For showing the successful evolution of aptamer pools, aptamer pools from round 4, 8, 12, and 16 of CTLA-4 selection were selected and analyzed. The binding affinity and specificity were measured by total binding assay coupled with RT-qPCR (as shown in FIG. 1, panel A) and flow cytometry (as shown in FIG. 1, panels B-I). These data indicated that both affinity and specificity were elevated along with the increase of SELEX rounds. For example, the affinity increased from 120.7 nM (Round 4) to 6.6 nM (Round 16) (as shown in FIG. 1, panel A). The non-specific binding of the aptamer pools were successfully reduced in later SELEX rounds (as shown in FIG. 1, panels B-I). These data suggested that our SELEX procedure worked efficiently in selecting high affinity and specific aptamers. After 16 rounds of selection, the aptamer pools were sequenced.

Figure 2:
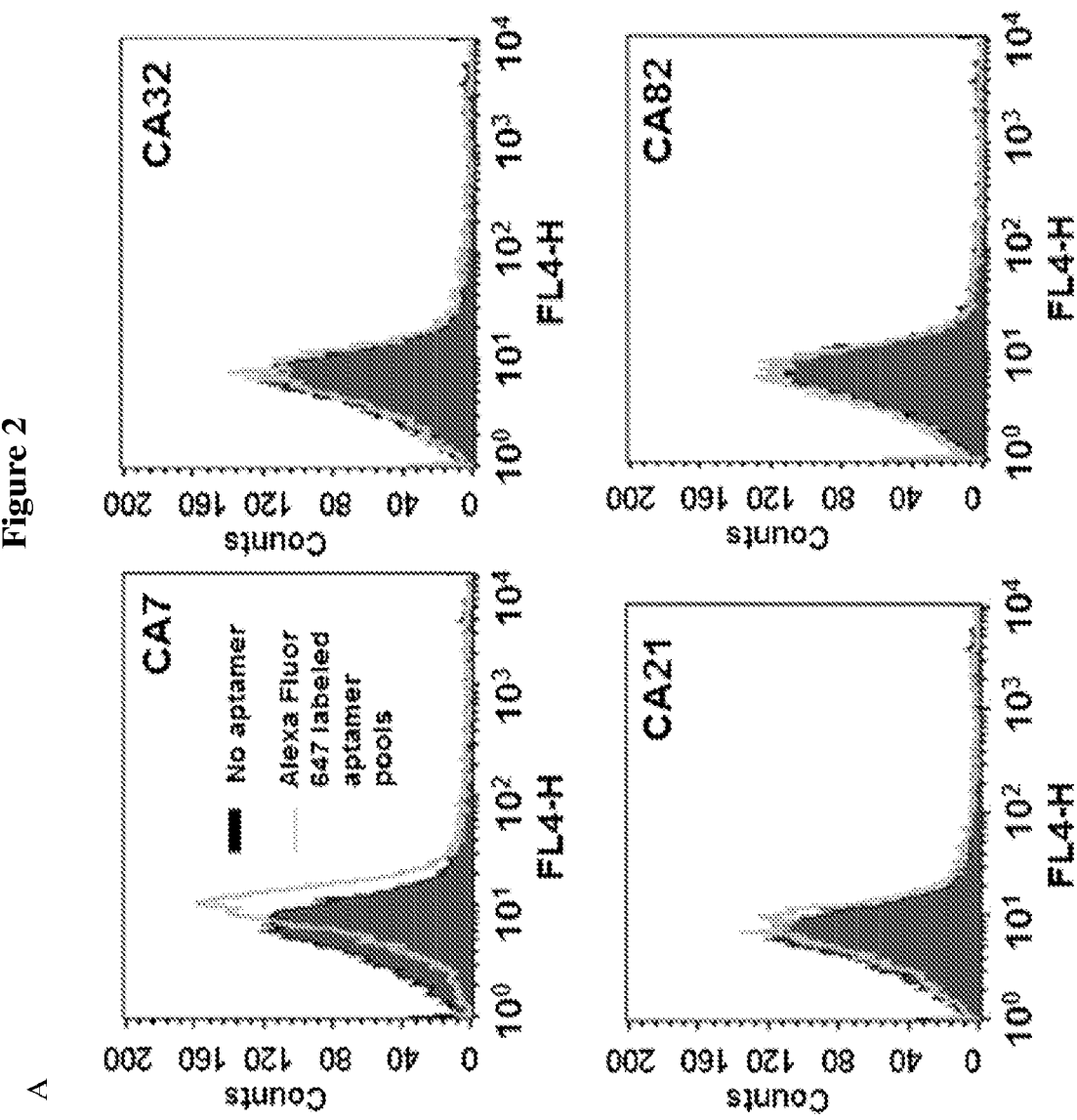
FIG. 2 shows diagrams of CTLA-4-binding activities of aptamers selected by SELEX evolution. Panels A and B are FACS analysis diagrams showing the binding activities of selected aptamers to CTLA-4 expressed on wild-type 293T cells. Panel A shows 293T cells that were transfected with CTLA-4 expressing plasmid and panel B shows non-transfected 293T cells, which serve as negative control. The cells of panel A and panel B were incubated with 10 nM of AlexaFluor 647 labeled CA7, CA21, CA32 and CA82 aptamer as indicated. After washing away the unbounded aptamer, the fluorescent signals were measured by flow cytometry and the results of wild-type 293T cells are shown in panel A. The results for CTLA-4 expressing wild-type 293T cells are shown in panel B. Panels C, D, E and F show the CTLA-4 binding affinity of the aptamers CA7, CA21, CA32 and CA82, respectively. The four aptamers were selected and characterized for their binding affinity against CTLA-4 expressing cells. These aptamers were first synthesized and followed by 2-fold serial dilution which started from 250 nM. Six dosage points were analyzed after incubation of the selected pool with CTLA-4 stably expressed 293 cells. The dissociation constant for CA7, CA21, CA32 and CA82 were 51.48 nM, 11.84 nM, 61.75 nM and 36.51 nM, respectively.
Figure 2:
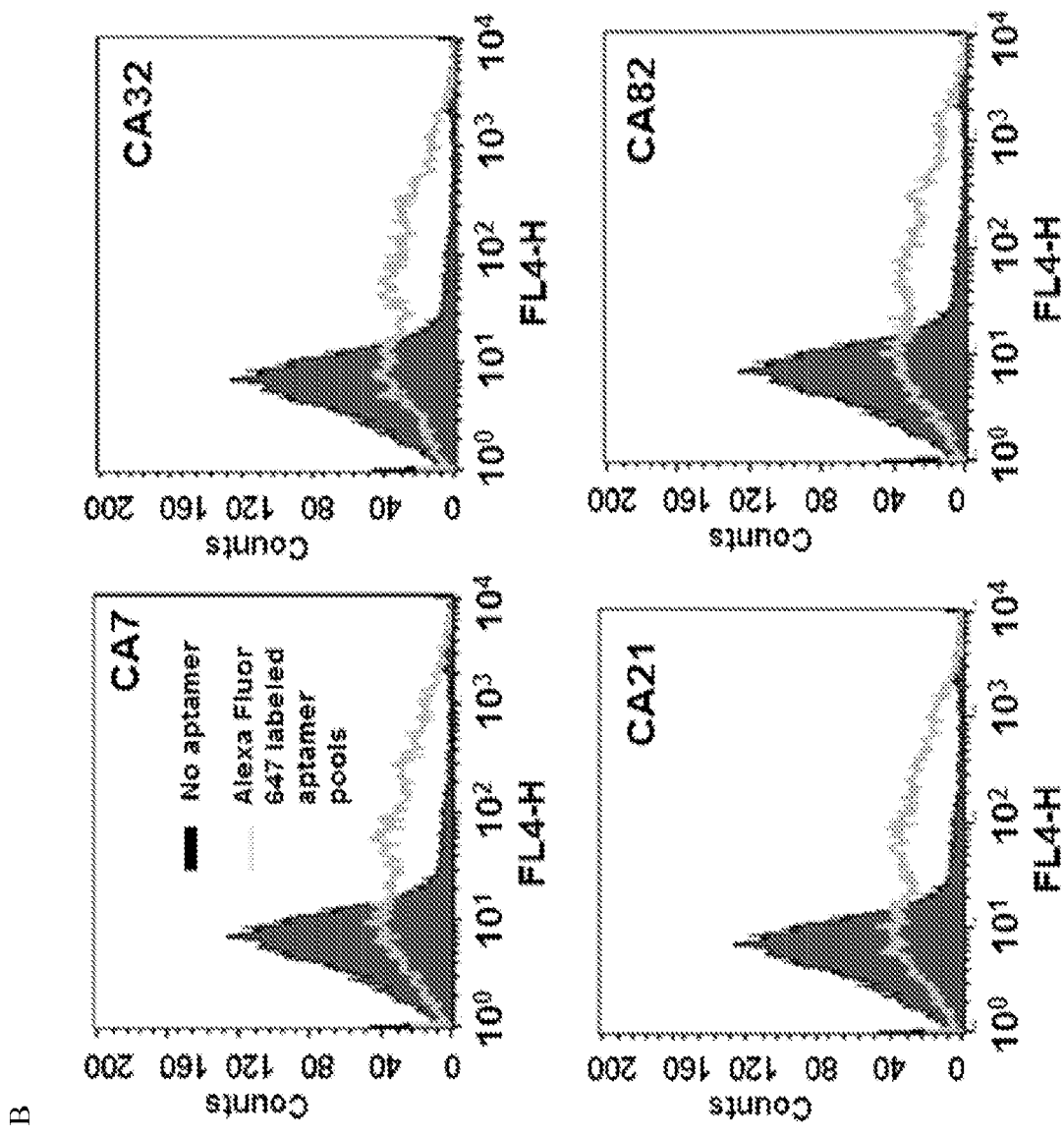
Figure 2:
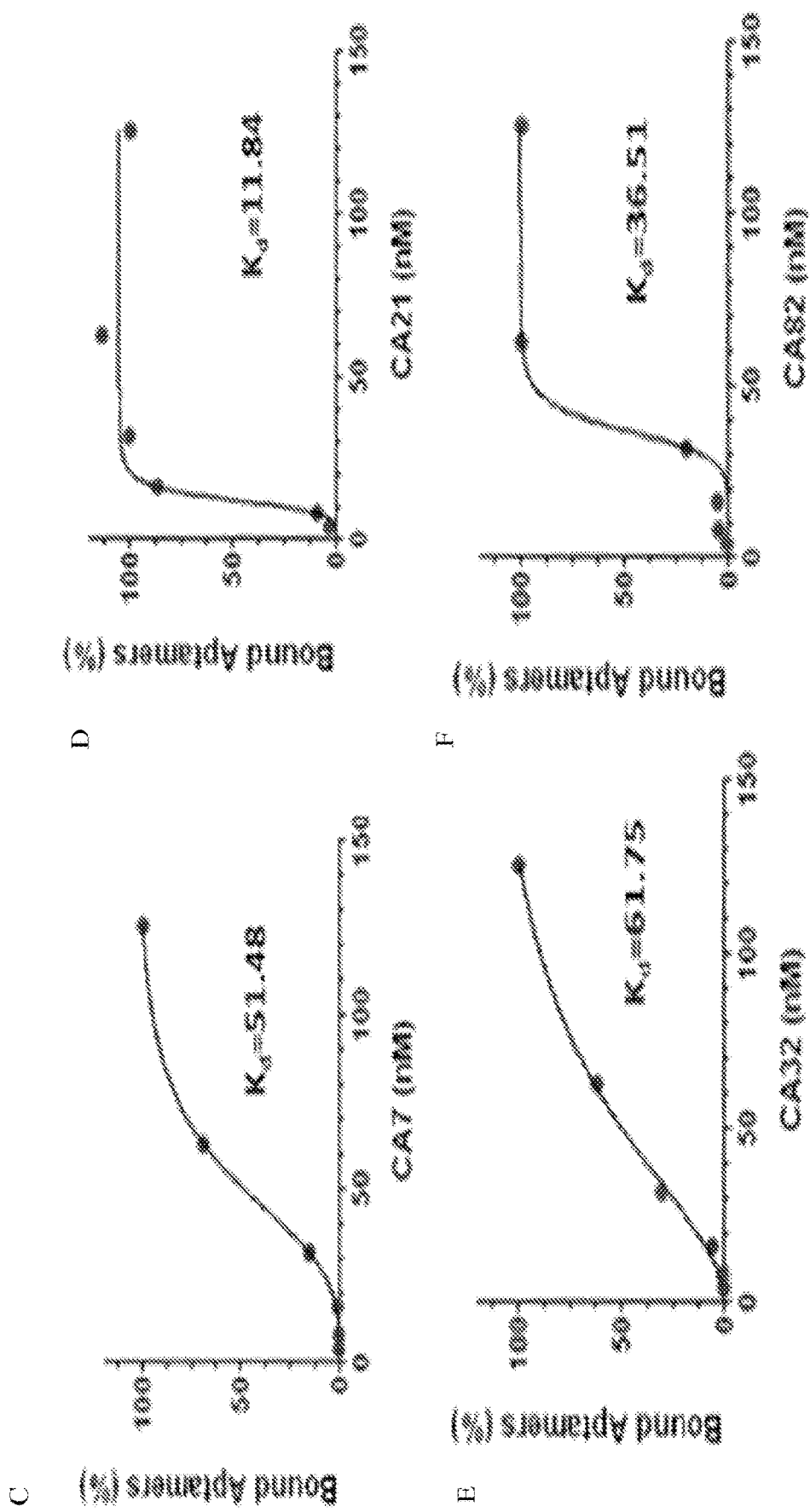

Example 2: Isolated Aptamers Specifically Recognized CTLA-4-Expressed Cells with High Affinity Four aptamers (CA7, CA21, CA32 and CA82) isolated by the method described in Example 1 were selected by their higher structural stability. The binding specificity of these four aptamers were analyzed by flow cytometry. All four of these apatmers specifically recognized CTLA-4-expressing cells, except a relatively low non-specific binding signal in CA7 against wild type 293 cells (FIG. 2, panels A and B). This data suggested that a specific aptamer against CTLA-4-expressing cells was identified. The non-wave shape florescent signal of CTLA-4-expressing cells (FIG. 2, panel B) was due to transient transfection which caused large variation of CTLA-4 expression level. The binding affinity of these four aptamers were also identified as shown in FIG. 2, panels C-F.

The nucleic acid sequence of aptamers CA7, CA32, and CA82 is shown below.

```
CA7:
                                         (SEQ ID NO: 3)
TCCCTACGGCGCTAACGATGACTGGATGCAAAAATGCTGTGGGGTAGC
CACCGTGCTACAAC

CA32:
                                         (SEQ ID NO: 4)
TCCCTACGGCGCTAACGTCCACACTCAGAAAACAGAATAGGGGGTAG
CCACCGTGCTACAAC

CA82:
                                         (SEQ ID NO: 5)
TCCCTACGGCGCTAACCGATCGAAAATGTCCAGGGAGTTGTCTGTA
GCCACCGTGCTACAAC
```

The italicized regions refer to the primer sites and the boldfaced regions refer to the core regions of these anti-CTLA4 aptamers.

Example 3: CTLA-4 Antagonistic Aptamer Inhibited Tumor Growth In Vivo

Figure 3:
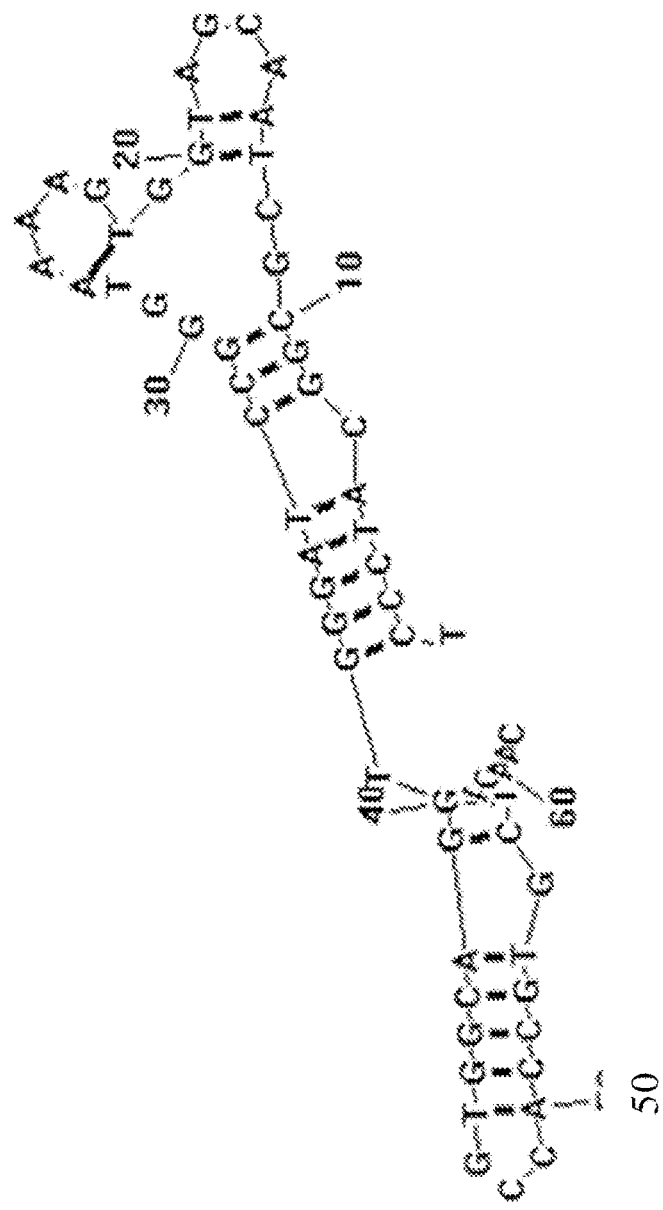
FIG. 3 includes diagrams showing the sequence of the anti-CTLA-4 aptamer in panel A, and the predicted secondary structure of the anti-CTLA-4 aptamer CA21 in panel B. In the nucleotide sequence of CA21 (SEQ ID NO:2) in panel A, the underlined G residues indicate the possible locus for forming G-quatruplex structures. The 16 grey nucleotides at the 5' and 3' ends indicate the 5' and 3' primer regions. The secondary structure of CA21 as determined by Mfold is shown in panel B, and the $\Delta G$ of this structure is $-10.6$.

After analyzing 50 isolated CTLA-4 aptamers, 5 aptamers that recognized binding site of B7-1 and B7-2 protein on CTLA-4 were identified. One of the aptamers, CA21, which cross-reacted with mouse CTLA-4, was selected for tumor inhibition assay in a syngeneic mice model. FIG. 3 shows the sequences (FIG. 3, panel A) and predicted secondary structure (FIG. 3, panel B) of the CA21 aptamer.

Figure 4:
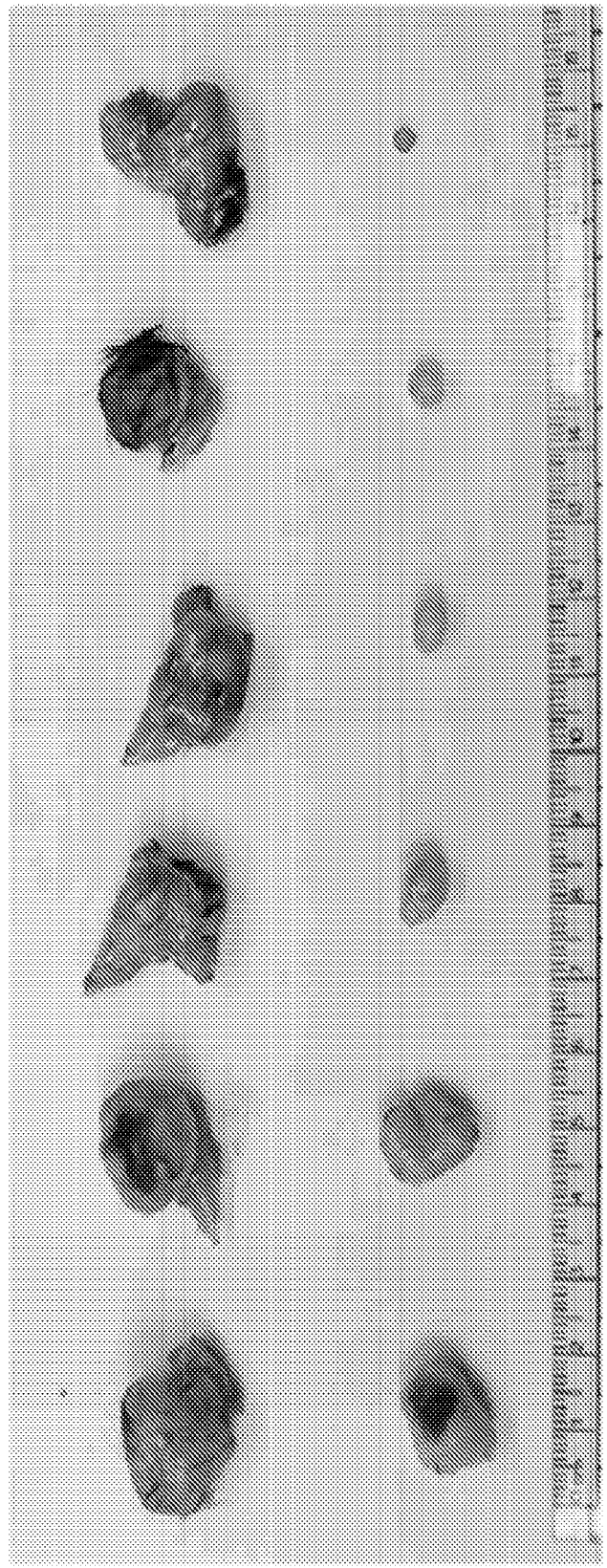
FIG. 4 includes diagrams showing the anti-cancer effect of the anti-CTLA-4 aptamer CA21. Panel A is a photo showing that a single injection of CA21 oligonucleotide suppressed lung tumor growth in TC-1 cells in a syngeneic mouse model. Mouse TC-1 lung cancer cells ($3 \times 10^5$) were subcutaneously transplanted into C57BL/6 mice. When the short axis of tumors reached 8 mm, 0.3 nmole CA21 in PBS or control PBS were injected into peritoneal spaces of the mice. The day of injection was recorded as Day 0 and tumor size were measured 2 times per week. Severe tissue reactions were observed grossly in control group (see top row of tumors in panel A) as compared to aptamer CA21 treatment (see bottom row of tumors in panel A). Panel B is a chart showing the means of tumor volumes in control and CA21-treated mice. Panel C is a chart showing the tumor growth rates in CA21-treated and PBS-treated mice. Tumor sizes were calculated by the formula: $(L \times D^2)/2$, in which L is long diameter, and D is short diameter. Panel D is a chart showing the body weights of mice treated with CA21 or PBS. Panel E is a chart showing the in vitro inhibition activity of CA21 on TC-1 cell growth.
Figure 4:
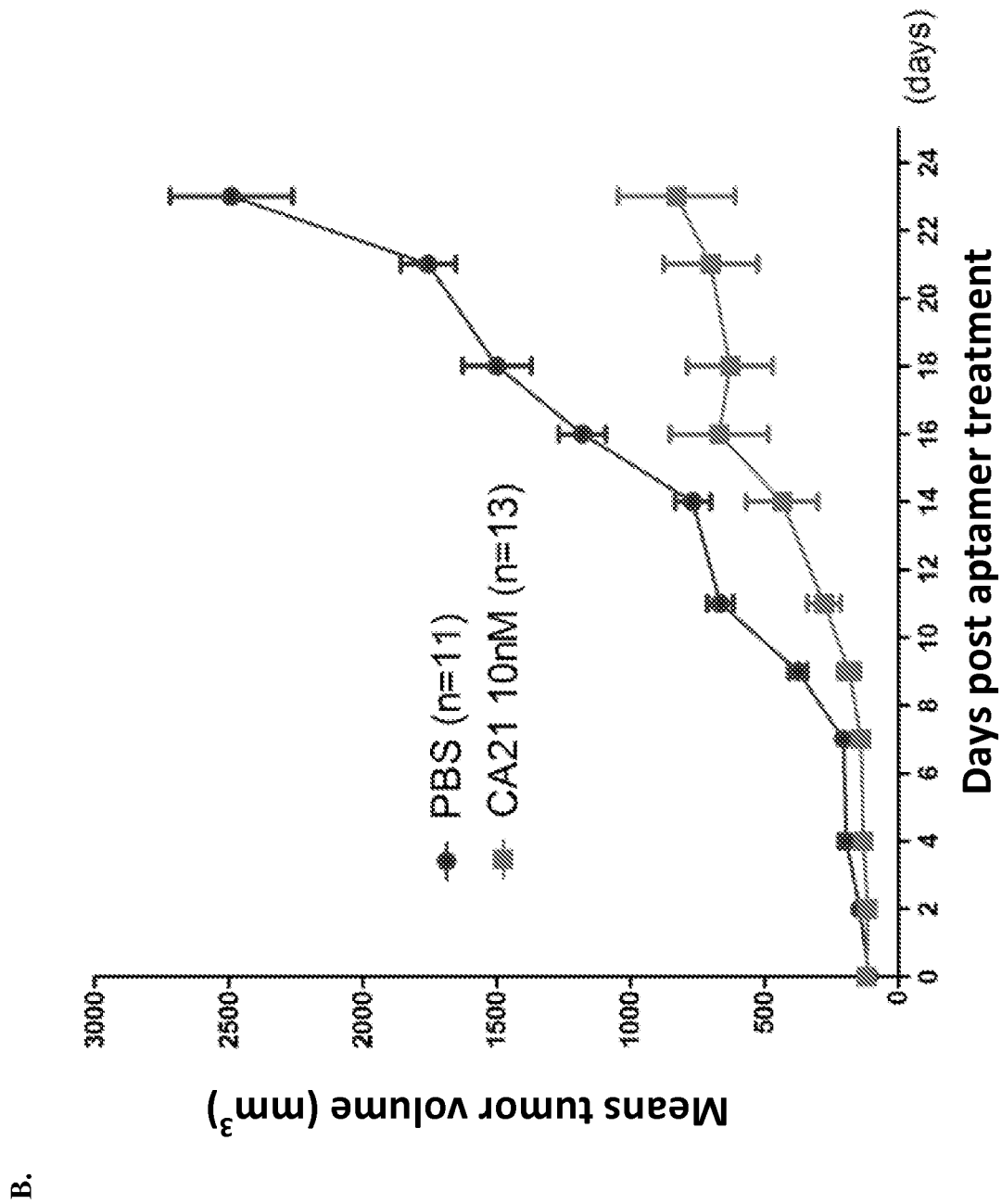
Figure 4:
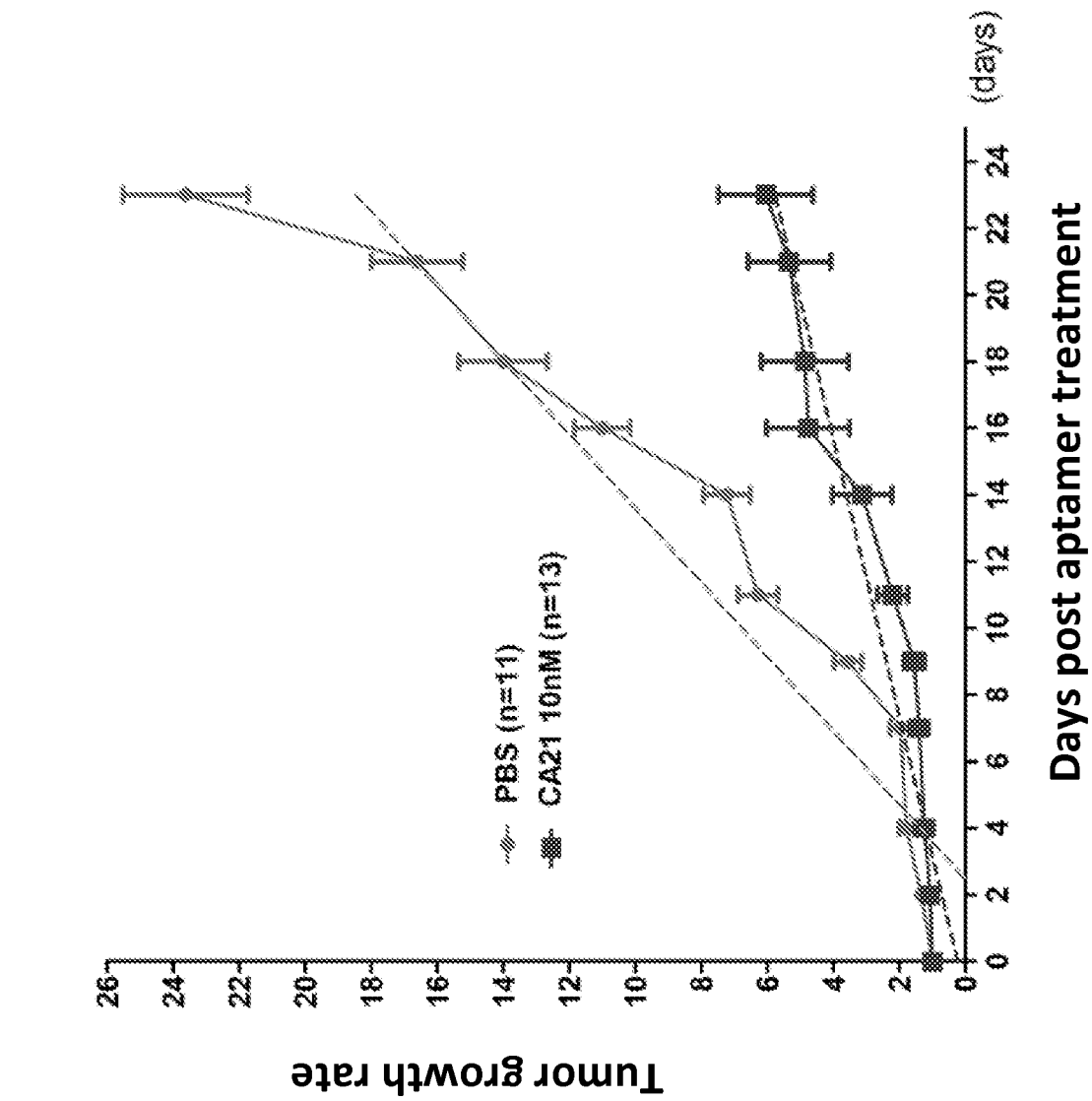
Figure 4:
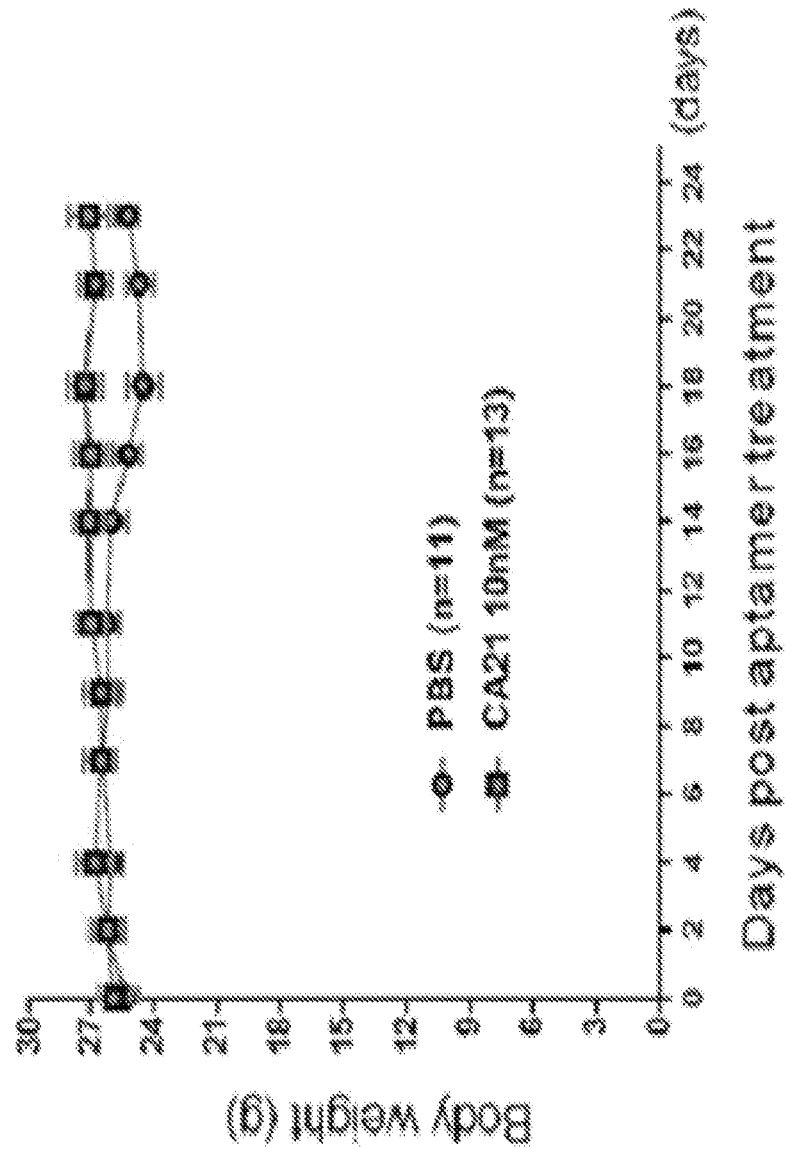
Figure 4:
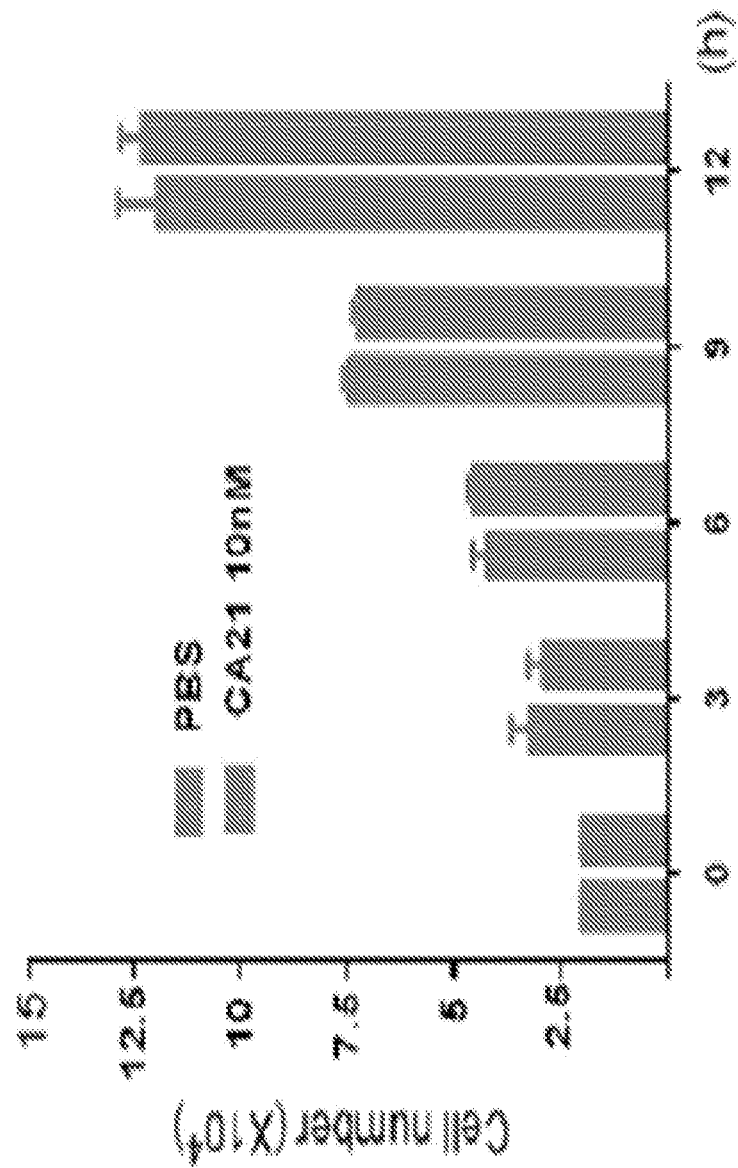

Mouse TC-1 lung cancer cells ($3\times10^5$) were subcutaneously transplanted into C57BL/6 mice. When the short axis of tumors reached 8 mm, 0.3 nmole CA21 in PBS or control PBS were injected into peritoneal spaces of the mice. The day of injection was recorded as Day 0 and tumor size were measured 2 times per week. The results indicated that CA21 can efficiently inhibit tumor growth compared to control PBS treatment control (FIG. 4, panel A). The tumor volume was monitored for 24 days and the tumor growth was reduced by over 70% following CA21 treatment (FIG. 4, panels B and C). On the contrary, CA21 treatment does not affect mouse body weight or in vitro tumor cell proliferation (FIG. 4, panels D and E). These data suggest that CA21 inhibits tumor cell growth by indirect mechanism.

Figure 5:
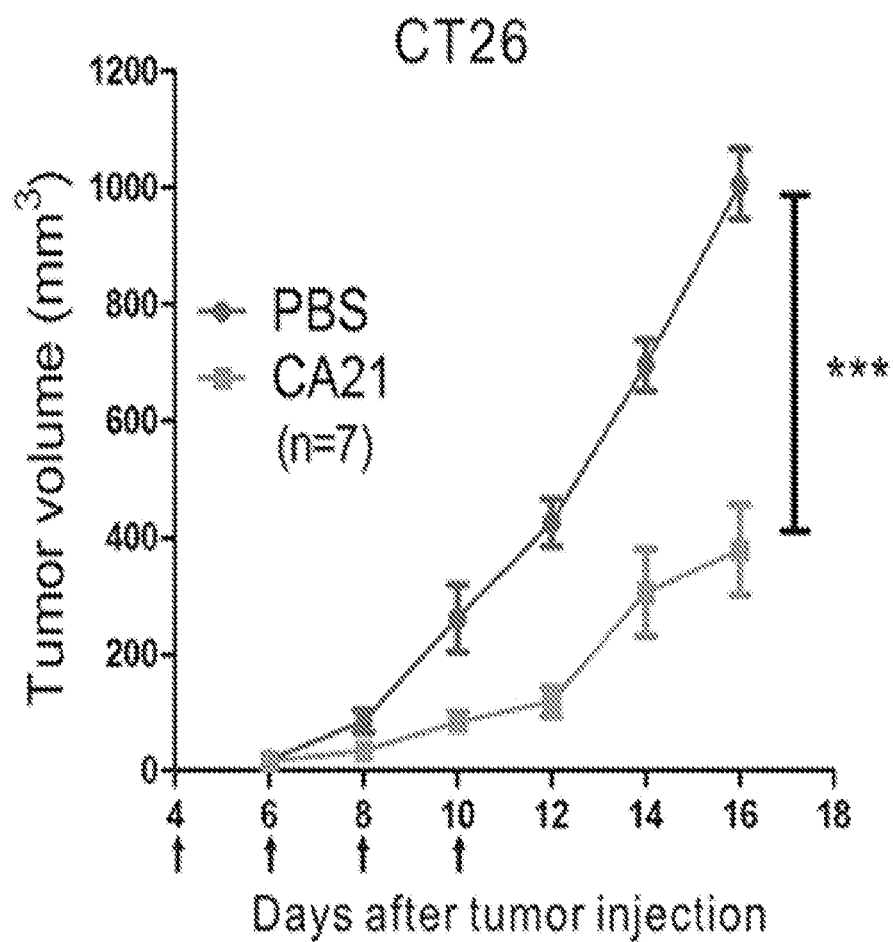
FIG. 5 includes diagrams showing the anti-cancer effect of the anti-CTLA-4 aptamer CA21 on CT26 colon cancer cells in a syngeneic mouse model. Panel A shows the tumor volume of BALB/c mice that were subcutaneously injected with CT26 colon cancer cells. After tumors reached 8 mm, 0.3 nmole of CA21 in PBS (squares) or control PBS (circles) was injected into the peritoneal spaces of the mice at days 4, 6, 8 and 10. The day of CT26 cell injection was recorded as Day 0 and tumor size was measured three times per week. The graph shows an approximate 70% reduction in tumor volume in mice treated with the anti-CTLA-4 aptamer CA21. Panel B shows the tumors from C57BL/6 mice treated with control PBS (see top row of tumors in panel B) or CA21 aptamer (see bottom row of tumors in panel B).
Figure 5:
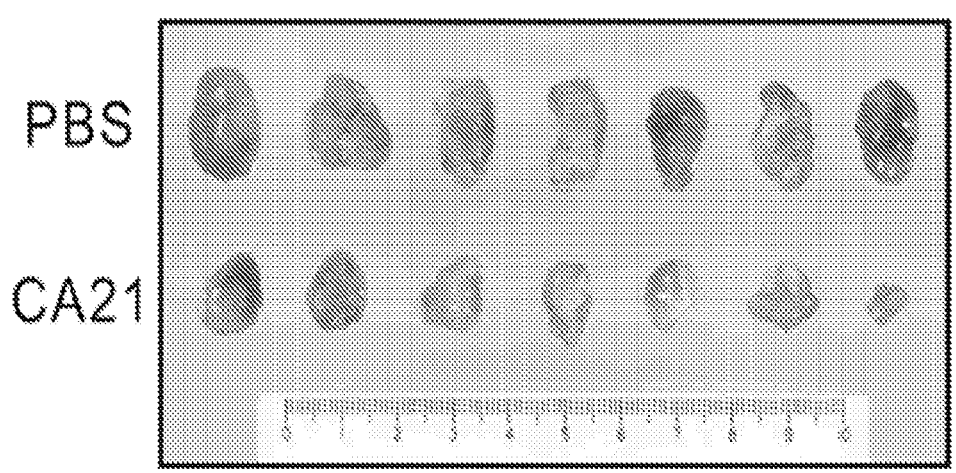

Example 4: CTLA-4 Antagonistic Aptamer Inhibited Tumor Growth in an In Vivo Syngeneic Mouse Model of Colon Cancer A syngeneic mouse model was used to demonstrate the inhibitory activity of the CTLA-4 antagonistic aptamer CA21 on the growth of colon cancer in vivo. Briefly, mouse CT26 colorectal cancer cells (ATCC CRL-2638) were subcutaneously transplanted into BALB/c mice at day 0 ($2\times10^5$ CT26 cells per mouse). After tumors reached 8 mm on the short axis, 0.3 nmole of CA21 in PBS or control PBS was injected into the peritoneal spaces of the mice. As shown in FIG. 5, panel A, the CT26 cell syngeneic mice were injected with the CA21 aptamer on days 4, 6, 8 and 10 (FIG. 5, panel A; arrows indicate injection times). Tumor size was measured three times per week. The formula used to calculate tumor size was $(L\times D^2)/2$, where L is the long diameter of the tumor, and D is the short diameter of the tumor. The tumor size in the CA21 treated mice was reduced by approximately 70% as compared to the tumor size of mice treated with control PBS (FIG. 5, panel B) at day 16 post tumor cell injection. These data indicate that the CA21 aptamer can be used to treat colon cancer.

Figure 6:
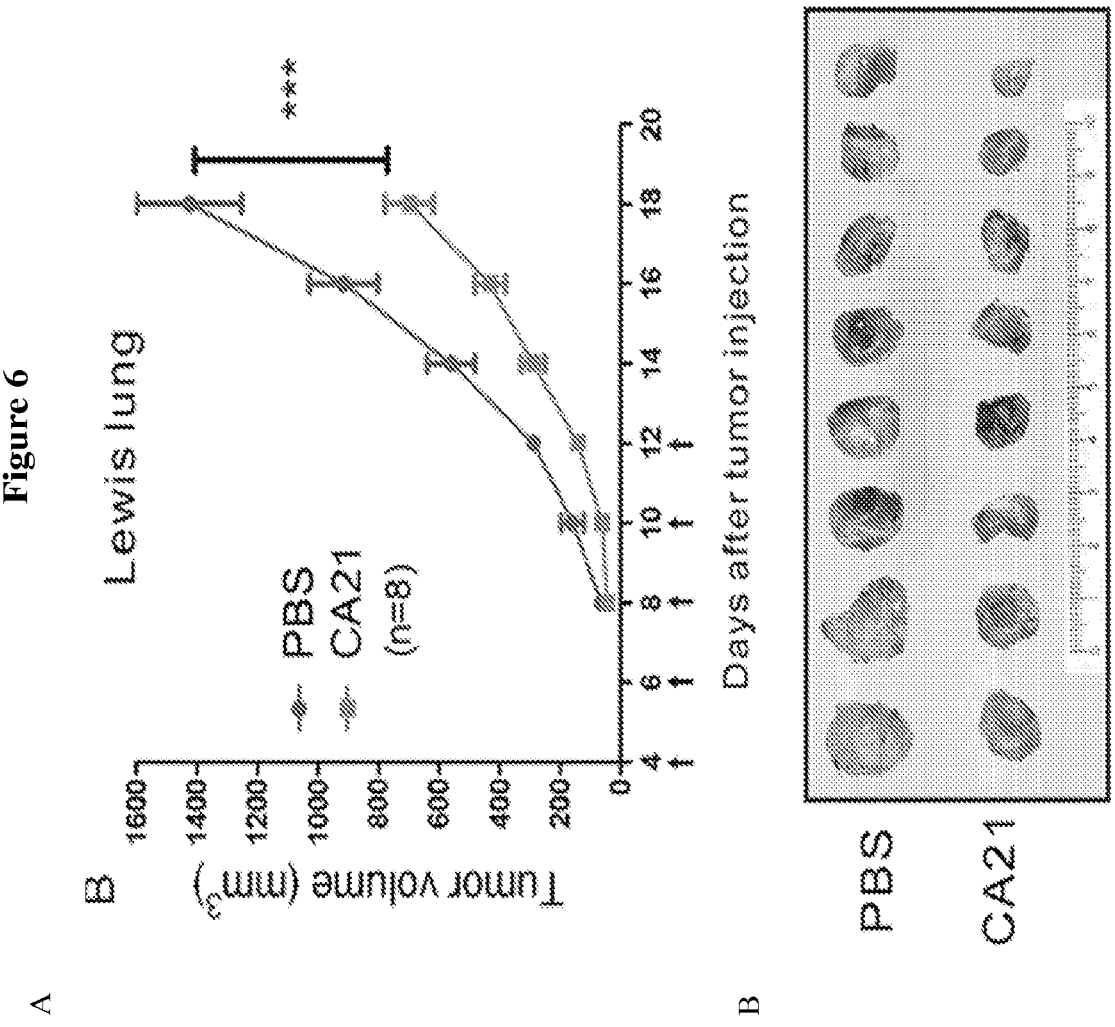
FIG. 6 includes diagrams showing the anti-cancer effect of the anti-CTLA-4 aptamer CA21 on Lewis lung cancer cells in a syngeneic mouse model. Panel A shows the tumor volume of C57B/6 mice that were subcutaneously injected with Lewis lung cancer cells. After tumors reached 8 mm, 0.3 nmole of CA21 in PBS (squares) or control PBS (circles) was injected into the peritoneal spaces of the mice at days 4, 6, 8, 10 and 12. The day of Lewis lung cell injection was recorded as Day 0 and tumor size was measured three times per week. The graph shows an approximate 50% reduction in tumor volume in mice treated with the anti-CTLA-4 aptamer CA21. Panel B shows the tumors from C57B/6 mice treated with control PBS (see top row of tumors in panel B) or CA21 aptamer (see bottom row of tumors in panel B).

Example 5: CTLA-4 Antagonistic Aptamer Inhibited Tumor Growth in an In Vivo Syngeneic Mouse Model of Lung Cancer A syngeneic lung cancer mouse model was used to demonstrate the inhibitory activity of the CTLA-4 antagonistic aptamer CA21 on the growth of lung cancer in vivo. Briefly, mouse Lewis lung cancer cells (ATCC, CRL1642) were subcutaneously transplanted into C57BL/6 mice at day 0 ($1\times10^5$ Lewis lung cells per mouse). After tumors reached 8 mm on the short axis, 0.3 nmole of CA21 in PBS or control PBS was injected into the peritoneal spaces of the mice. As shown in FIG. 6, panel A, the Lewis lung cell syngeneic mice were injected with the CA21 aptamer on days 4, 6, 8, 10 and 12 (FIG. 6, panel A; arrows indicate injection times). Tumor size was measured three times per week. The formula used to calculate tumor size was $(L\times D^2)/2$, where L is the long diameter of the tumor, and D is the short diameter of the tumor. The tumor size in the CA21 treated mice was reduced by approximately 50% as compared to the tumor size of mice treated with control PBS (FIG. 5, panel B) at day 18 post tumor cell injection. These data indicate that the CA21 aptamer can be used to treat lung cancer.

Example 6: Intravenous Administration of a Pegylated CTLA-4 Antagonistic Aptamer Inhibits Tumor Growth The inhibitory activity of a pegylated form of CA21 (CA21-PEG) on cancer cell growth in vivo was assessed in this study.

The CA21 aptamer was conjugated to polyethylene glycol (PEG) using maleimide. To generate CA21-PEG, a 3'-thiol CA21 aptamer (3 nmol) in 20 μL of 18 mM ammonium formate pH 4 was added to 30 nmol of PEG having a molecular weight of 40 KDa (1:5 reduced aptamer to PEG molar ratio). The mixture was mixed in a thiol and maleimide reaction at 37° C. After 1 hour, the mixture was subjected to polyacrylamide gel electrophoresis (PAGE) to isolate the CA21-PEG, which was extracted from the polyacrylamide gel using standard techniques. The molecular weight of PEG used was 40 KDa, which was attached to the 3' end of the CA21 aptamer.

Figure 7:
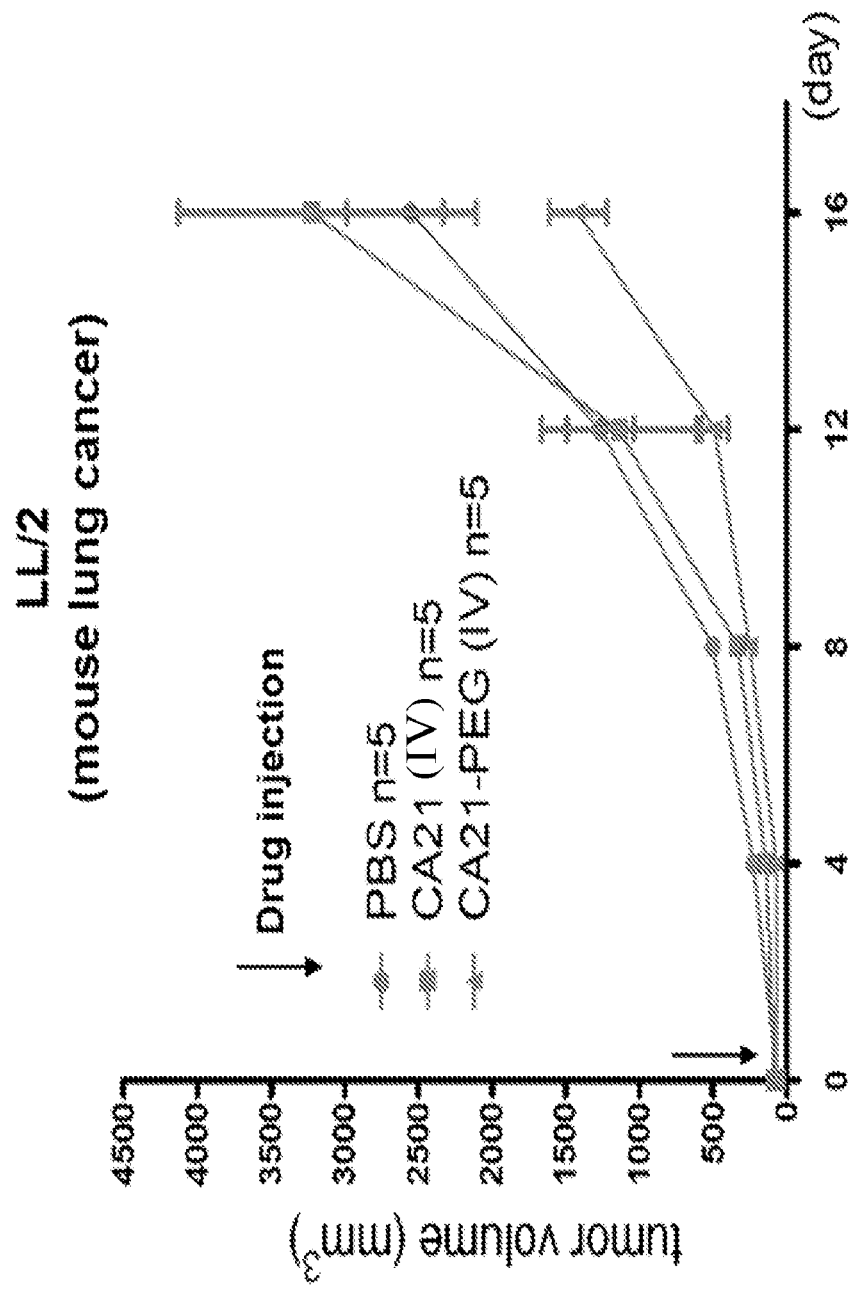
FIG. 7 is a graph showing a comparison of the anti-cancer effect between the CA21aptamer and the pegylated CA21 aptamer (CA21-PEG) on Lewis lung cancer cells in a syngeneic mouse model by intravenous injection. The graph shows the tumor volume of C57B/6 mice that were subcutaneously injected with Lewis lung cancer cells. After tumors reached 8 mm, 0.3 nmole of CA21 in PBS (squares), 0.3 nmole of CA21-PEG in PBS (triangles) or control PBS (circles) was injected intravenously into the mice by tail-vein injection. The day of Lewis lung cell injection was recorded as Day 0 and tumor size was measured two times per week. The graph shows an approximately 50% reduction in tumor volume in mice treated with the pegylated CA21aptamer (CA21-PEG) as compared to the CA21 aptamer.

The anti-cancer activity of CA21-PEG was determined in a syngeneic lung cancer mouse model by intravenous administration. Lewis lung cancer cells (ATCC, CRL1642) were subcutaneously transplanted into C57BL/6 mice at day 0 ($1\times10^5$ Lewis lung cells per mouse) After tumors reached 8 mm on the short axis, one dose of 0.3 nmole of CA21 in PBS, 0.3 nmole of CA21-PEG in PBS, or control PBS was injected into the tail-vein of the mice. Tumor size was measured two times per week. The formula used to calculate tumor size was $(L\times D^2)/2$, where L is the long diameter of the tumor, and D is the short diameter of the tumor. The tumor size in the CA21-PEG treated mice was reduced by approximately 50% as compared to the tumor size of mice treated with CA21 (FIG. 7) at day 16 post tumor cell injection. These data indicate that the pegylated CA21 aptamer, CA21-PEG can be used to treat cancer by intravenous administration.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A nucleic acid aptamer that binds CTLA-4, wherein the aptamer comprises the nucleic acid sequence selected from the group consisting of:

(i)
(SEQ ID NO: 1)
GATGGTGAAAATGGGCCTAGGGTGGACGGT;

(ii)
(SEQ ID NO: 6)
GATGACTGGATGCAAAAATGCTGTGGGGTA;

(iii)
(SEQ ID NO: 7)
GTCCACACTCAGAAAACAGAATAGGGGGTA;
and (iv)
(SEQ ID NO: 8)
CGATCGAAAATGTCCAGGGAGTTGTCTGTA.

2. The nucleic acid aptamer of claim 1, wherein the aptamer consists of a nucleic acid sequence selected from the group consisting of:

(a)
(SEQ ID NO: 2)
TCCCTACGGCGCTAACGATGGTGAAAATGGGCCTAGGGTGGACGGTGCC
ACCGTGCTACAAC;

(b)
(SEQ ID NO: 3)
TCCCTACGGCGCTAACGATGACTGGATGCAAAAATGCTGTGGGGTAGCCA
CCGTGCTACAAC;

(c)
(SEQ ID NO: 4)
TCCCTACGGCGCTAACGTCCACACTCAGAAAACAGAATAGGGGGTAGCC
ACCGTGCTACAAC;
and (d)
(SEQ ID NO: 5)
TCCCTACGGCGCTAACCGATCGAAAATGTCCAGGGAGTTGTCTGTAGCCA
CCGTGCTACAAC.

3. The nucleic acid aptamer of claim 1, wherein the nucleic acid aptamer is conjugated with polyethylene glycol (PEG).

4. The nucleic acid aptamer of claim 3, wherein the PEG is conjugated to the 3' end of the nucleic acid aptamer.

5. The nucleic acid aptamer of claim 3, wherein the PEG has a molecular weight ranging from 30 kDa to 50 kDa.

6. The nucleic acid aptamer of claim 5, wherein the PEG has a molecular weight of 40 kDa.

7. A pharmaceutical composition, comprising the nucleic acid aptamer of claim 1 and a pharmaceutically acceptable carrier.

8. A method for treating cancer, comprising administering to a subject in need thereof an effective amount of the pharmaceutical composition of claim 7.

9. The method of claim 8, wherein the subject is a human patient having, suspected of having, or at risk for cancer.

10. The method of claim 8, wherein the cancer is lung cancer, melanoma, colorectal cancer, or renal-cell cancer.

11. The method of claim 8, wherein the pharmaceutical composition is administered to the subject intravenously.

12. A method of enhancing immune activity, the method comprising administering to a subject in need thereof an effective amount of the pharmaceutical composition of claim 7.

13. The method of claim 12, wherein the subject is a human patient having, suspected of having, or at risk for cancer.

14. The method of claim 13, wherein the cancer is lung cancer, melanoma, colorectal cancer, or renal-cell cancer.

15. The method of claim 12, wherein the subject is a human patient having or suspected of having HIV infection.

16. The method of claim 12, wherein the amount of the pharmaceutical composition is effective in increasing T cell activation.

17. The method of claim 12, wherein the pharmaceutical composition is administered to the subject intravenously.

* * * * *

SEQUENCE LISTING

```
<160> NUMBER OF SEQ ID NOS: 8

<210> SEQ ID NO 1
<211> LENGTH: 30
<212> TYPE: DNA
<213> ORGANISM: Artificial Sequence
<220> FEATURE:
```

<223> OTHER INFORMATION: Synthetic Polynucleotide

<400> SEQUENCE: 1
gatggtgaaa atgggcctag ggtggacggt                                          30

<210> SEQ ID NO 2
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 2
tccctacggc gctaacgatg gtgaaaatgg gcctagggtg acggtgccca ccgtgctaca         60
ac                                                                        62

<210> SEQ ID NO 3
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 3
tccctacggc gctaacgatg actggatgca aaatgctgt ggggtagcca ccgtgctaca          60
ac                                                                        62

<210> SEQ ID NO 4
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 4
tccctacggc gctaacgtcc acactcagaa aacagaatag ggggtagcca ccgtgctaca         60
ac                                                                        62

<210> SEQ ID NO 5
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 5
tccctacggc gctaaccgat cgaaaatgtc cagggagttg tctgtagcca ccgtgctaca         60
ac                                                                        62

<210> SEQ ID NO 6
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 6
gatgactgga tgcaaaaatg ctgtggggta                                          30

<210> SEQ ID NO 7
<211> LENGTH: 30
<212> TYPE: DNA
<213> ORGANISM: Artificial Sequence

```
<220> FEATURE:
<223> OTHER INFORMATION: Synthetic Polynucleotide

<400> SEQUENCE: 7
gtccacactc agaaaacaga ataggggta                                              30

<210> SEQ ID NO 8
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 8
cgatcgaaaa tgtccaggga gttgtctgta                                             30
```